United States Patent [19]

Konrad et al.

[11] Patent Number: 4,752,467
[45] Date of Patent: Jun. 21, 1988

[54] HAIR TREATMENT AGENT AND METHOD FOR IMPROVING THE CONDITON OF HAIR

[75] Inventors: Eugen Konrad, Darmstadt; Herbert Mager, Fribourg; Dietrich Hoch, Pfungstadt, all of Fed. Rep. of Germany

[73] Assignee: Wella Aktiengesellschaft, Darmstadt, Fed. Rep. of Germany

[21] Appl. No.: 16,988

[22] Filed: Feb. 17, 1987

Related U.S. Application Data

[63] Continuation of Ser. No. 714,110, Mar. 20, 1985, abandoned, which is a continuation of Ser. No. 413,339, filed as PCT EP82/00003, filed Jan. 12, 1982, published as WO82/02337, Jul. 22, 1982, abandoned.

[30] Foreign Application Priority Data

Jan. 15, 1981 [DE] Fed. Rep. of Germany ....... 3101011

[51] Int. Cl.$^4$ ........................ A61K 7/075; A61K 7/08; A61K 31/205
[52] U.S. Cl. ..................................... 424/70; 514/556
[58] Field of Search ........................... 514/556; 424/70

[56] References Cited

U.S. PATENT DOCUMENTS

| | | | |
|---|---|---|---|
| 2,794,045 | 5/1957 | Beoufour | 260/501.13 |
| 3,984,538 | 10/1976 | Korkis | 424/70 |
| 3,996,146 | 12/1976 | Tarasov et al. | 424/70 |
| 4,190,064 | 2/1980 | Gordon et al. | 424/70 |

FOREIGN PATENT DOCUMENTS 1007957  5/1957  Fed. Rep. of Germany .

OTHER PUBLICATIONS

"Compatability Measurements on Human Hair", by Mario L. Garcia and Jose Diaz, *Journal of the Society of Cosmetic Chemists*, Sep. 1976, vol. 27 (pp. 379–398).

Primary Examiner—Nicky Chan
Assistant Examiner—Wendy B. Davis
Attorney, Agent, or Firm—Michael J. Striker

[57] ABSTRACT

The subject matter of the invention is an agent and a method for improving the condition of hair on the basis of a combination of 0.1 to 25.0% by weight of trimethyl ammonia acetate betaine of the formula $(CH_3)_3N^{\oplus}$—$CH_2$—$COO^{\ominus}$ and 0.1 to 10.0% by weight of at least one aliphatic organic acid as a hair conditioning component. Preferred forms of preparations are a hair conditioning rinse, a hair conditioning emulsion, a hair treatment kit, or a hair strengthener.

2 Claims, No Drawings

HAIR TREATMENT AGENT AND METHOD FOR IMPROVING THE CONDITON OF HAIR

This application is a continuation of application Ser. No. 714,110, filed Mar. 20, 1985, now abandoned, which in turn is a continuation of application Ser. No. 413,339 filed as PCT EP82/00003, filed Jan. 12, 1982, published as WO82/02337, Jul. 22, 1982, now abandoned.

BACKGROUND OF THE INVENTION

Due to frequent bleaching, permanent and dyeing, but also due to frequent washing of hair with degreased tensides, a damage of the hair structure occurs. The hair becomes brittle and it loses its luster. Furthermore, the hair is electrostatically charged during combing and the roughened hair surface causes felting as well as knotting of the hair. Thereby, the combing is made more difficult.

Therefore, hair treatment agents with a combing improvement and managing effect have obtained a considerable importance. Such agents are distributed in the still wet hair after hair washing, for example, frequently in form of a clear managing rinse, but also in form of an emulsion as so-called creme rinses, which one will let act for a few minutes or up to an hour and thereafter rinsing it with water.

As active substances for improving the hair structure mainly cationic tensides are used, in particular, quaternary ammonium compounds, like cetyltrimethylammonium chloride in combination with different wax like additives, as for example, petroleum jelly, fat alcohols and fat acid esters.

However, hair treatment agents on the basis of the aforementioned conditioning active substances only show sufficient results when treating dry and brittle hair. They are less well suitable for the treatment of quickly refattening hair, since due to its use the naturally refattening of the hair is still increased, whereby the stability of the hair style is impaired.

The causes of the severe refattening of the hair are, on the one hand, the residues of the hair treatment agent which remain in the hair after rinsing and, on the other hand, the cationic emulsifiers contained in these agents. The cationic emulsifiers which are adsorbed by the hair cause a hydrophobation of the hair surface, whereby the secretions of the sebaceous gland can more quickly distribute in the hair. Moreover, the cationic emulsifiers do not permit a working into any of the shampoos ir hair dye agents, for example, because of their incompatability with anionic tensides in hair treatment agents with a content of these tensides.

SUMMARY OF THE INVENTION

Accordingly, the object of the invention consists of making available a hair treatment method on the basis of better suitable hair conditioning active substances and thereby to eliminate the aforementioned disadvantages.

It was found that the object of the invention can be fullfilled in an excellent manner with a hair treatment agent, characterized in that it contains a combination of (a) 0.1 to 25.0% by weight betain =trimethylammonioacetate of the formula

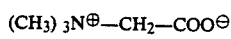

and (b) 0.1 to 10.0% by weight of at least one aliphatic acid.

While no noticeable hair conditioning characteristics are ascertainable with hair treatment agents on the sole basis of betain or on the sole basis of an aliphatic organic acid, the inventive hair treatment has a good combability improving effect on the basis of a synergistic combination of betain and an aliphatic organic acid without placing any stress on the hair. Furthermore, they act astringent and disentangling to the hair, smooth the hair surface and improve the touch of the hair.

DETAILED DESCRIPTION OF THE PREFERRED EMBODIMENTS

For making the agents in accordance with the subject application one naturally can use, in addition to the pure betaine the betaine in any other given commercial form, for example, as a betainemonohydrate.

Examples for suitable aliphatic organic acids described in the subject agents are in particular water or water-alcohol soluble aliphatic organic acids, like citric acids, tartaric acid, lactic acid, pimelic acid and glyoxylic acid.

The agents in accordance with the invention should contain the betaine in particular in a concentration of 3.0 to 15.0% by weight, while the aliphatic organic acids, of which the citric acid is preferred, is contained alone or in an admixture, in particular in a quantity of 0.1 to 5.0% by weight.

The hair treatment agents described in the application may be present in any given prepared form available for the hair treatment, as for example, in form of a lotion, emulsion or a gel. Preferred preparations are hair rinses, hair conditioning emulsions, hair conditioning treatments, hair strengtheners or shampoos. However, the inventive hair treatment agents may be present as a hair dye agent, hair coloring agent or a fixing agent for the hair deformation.

These are preparations which remain on the hair for a shorter or longer duration depending on their purpose for application. Due to their content of the described active substance combination betaine/aliphatic organic acid a simultaneous conditioning of the treated hair is obtained. However, particularly preferred are preparations which mainly or exclusively serve the purpose to improve the condition of the hair structure.

The composition of these cosmetic preparations represents a mixture of the conditioning active combination of betaine/aliphatic organic acid with the further usual components for hair treatment agents.

As usual components of hair treatment agents the following components are taken into consideration, in particular, water, alcohols like, for example, ethanol, n-propanol, i-propanol multivalent alcohols, like glycerin and propylene glycol, anionic, cationic, amphoteric or nonionogenic tenside, like fat alcohol sulfates, fat alcohol ether sulfates, alkyl sulfonates, fat acid alkyl trimethyl ammonium salts, oxethiolized fat alcohols, oxethiolized nonylphenols, fat acid alkanolamides, furthermore natural, modified natural or synthetic polymers, as for example, shellac, alginates, gelatins, pectins, cellulose derivatives, chitosan, polyvinylpyrrolidone, polyvinyl acetate, acrylic acid or methacrylic acid polymerisates, basic polymerisates of esters from acrylic acids or methacrylic acid with amino alcohols, respectively the salts or quaternisation products of these basic polymerisates, polyacrylonitrile as well as copolymeristates from such compounds, like polyvinylpyrrolidone vinyl acetate, furthermore thickeners, like fat alcohols, fat acid esters, starch, cellulose derivatives, liquid and solid paraffins, isoparaffins, vaseline, wool wax and fatty acids as well as conditioning substances, like lanolin derivatives, cholesterine and pantothene acid, furthermore coloring agents, pigments, perfume oils, antioxidants, conserving agents, as for example, formaldehyde and salicylic acid.

In the inventive method for improving the condition of hair, the hair is brought into contact with a hair treatment agent, in particular with a hair conditioning rinse, characterized in that it contains a combination of
(a) 0.1 to 25.0% by weight betaine and
(b) 0.1 to 10.0% by weight of at least an aliphatic organic acid, at a temperature of about 15° to 60° C.

The hair conditioning effective betaine salts, for example, the betaine citrate, which is present in the inventive hair treatment agents is soluble in water or in water alcohol mixtures and is physiologically completely harmless, even at a very high concentration.

Furthermore, it had been shown surprisingly that thin liquid emulsions with a content of 10% by weight betaine and 2% by weight citric acid can be made without any problems despite of this high electrolyte content, by a suitable election of the wax components and the emulsifiers.

Furthermore, the described synergistic effective combination of betaine and an aliphatic organic acid can be worked into preparations with a content of anionic, cationic, nonionogenic or amphoteric tensides without precipitation.

The combination of betaine and an aliphatic organic acid contained in these hair treatment agents acts in these preparations antioxidative and as a buffer. In addition, a noticeable hair strengthening effect is obtained with hair strenghteners which have a content of at least 1% by weight betaine and at least 0.2% of an aliphatic organic acid, without the addition of a resin. Therefore, the combination betaine/aliphatic organic acid can replace the usually required resin in hair strengtheners.

An important advantage of the inventive hair treatment is finally its substantially improved eye and skin compatibility, in contrast to agents on the basis of usually cationic hair conditioning active substances, as for example, fat acid alkyl trimethyl ammonium salts.

The following examples will explain the subject matter of the invention in more detail.

EXAMPLES

EXAMPLE 1

| Hair conditioning rinse | |
|---|---|
| 10.0 g | betainemonohydrate |
| 2.0 g | tartaric acid and/or citric acid, free of water |
| 0.1 g | formaldehyde, 35% percent |
| 87.9 g | water, completely desalted |
| 100.0 g | |

This hair conditioning rinse is well distributed on the towel dry porous hair, after the hair is washed, it is left to act for a few minutes and is subsequently washed out with water. The hair is noticeably less felted and better combable.

EXAMPLE 2

| Hair conditioning rinse | |
|---|---|
| 10.0 g | betainemonohydrate |
| 2.0 g | citric acid, free of water |
| 0.1 g | formaldehyde, 35% percent |
| 7.0 g | isoparaffin |
| 80.9 g | water, completely desalted |
| 100.0 g | |

This hair conditioning rinse which consists of two liquid phases is shook shortly before use and is then used on lusterless and porous hair as in example 1. After the treatment the hair is easily combable and pliable.

EXAMPLE 3

| Hair conditioning emulsion | |
|---|---|
| 10.0 g | betainemonohydrate |
| 5.0 g | citric acid, free of water |
| 2.6 g | mixture of 50% cetyl alcohol and and 50% stearyl alcohol, hardening point: 48–52° C. |
| 0.5 g | mixture of 50% sodium cetyl sulfate and 50% sodium stearyl sulfate |
| 1.5 g | wool wax alcohol |
| 0.9 g | glycerin-mono-stearatpalmitate (85 percent 1-monoglyceride; 10% percent 2-monoglyceride; HLB-value: 4.5; acid number: max. 1.5; saponification number: 163–170; iodine number: max. 3) |
| 0.2 g | p-hydroxybenzo acid methyl ester |
| 0.2 g | salicylic acid |
| 0.5 g | perfume oil |
| 78.6 g | water |
| 100.0 g | |

After washing the hair, the hair conditioning emulsion is distributed in a severely felted very porous hair. Already during application one can notice a disentangling of the hair. After a short action time, the hair is rinsed with warm water. With this treatment a very smooth, cosmetic pleasant touch of the hair is obtained and a very good wet combability.

EXAMPLE 4

| Hair strengthener | |
|---|---|
| 0.5 g | betainemonohydrate |
| 0.1 g | citric acid, free of water |
| 40.0 g | isopropanol |
| 2.0 g | copolymer made of 60% vinylpyrrolidone and 40% vinyl acetate, in powder form |
| 0.5 g | perfume oil |
| 56.9 g | water, completely desalted |
| 100.0 g | |

This hair strengthener is applied evenly onto the towel dry hair, after the washing of the hair. Subsequently, the hair is rolled on set rollers. After drying the hair, which advantageously can be performed with the aid of a hair dryer at about 40°–60° C., a good hair strengthening, an improved stability of the hair style and a very pliable touch of the hair can be noticed.

EXAMPLE 5

| Hair color strengthener | |
|---|---|
| 0.5 g | betainemonohydrate |
| 0.1 g | citric acid, free of water |

| Hair color strengthener | |
|---|---|
| 0.1 g | coloring substance acid brown 4 (color index No. 14 805) |
| 2.0 g | copolymer made of 60% vinylpyrrolidone and 40% vinyl acetate, in powder form |
| 40.0 g | isopropanol |
| 0.5 g | perfume oil |
| 56.8 g | water, completely desalted |
| 100.0 g | |

This hair coloring strengthener is uniformly applied on towel dry blonde human hair, after washing the hair. Subsequently the hair is rolled on wash and set rollers. After drying the hair, a good hair strengthening, an improved stability of the hair style and a very pliable touch of the hair can be noticed. Furthermore, the hair has a reddish-blonde coloration.

EXAMPLE 6

| Hair strengthener | |
|---|---|
| 2.5 g | betaine |
| 0.5 g | citric acid, free of water |
| 40.0 g | isopropanol |
| 0.5 g | perfume oil |
| 56.5 g | water, completely desalted |
| 100.0 g | |

This hair strengthener is applied onto the towel dry hair, after washing the hair. Subsequently, the hair is rolled on set rollers. After drying the hair, a good hair strengthening and an improved stability of the hair style can be noticed, although no resin is present in the hair strengthener.

EXAMPLE 7

| Shampoo | |
|---|---|
| 8.0 g | betainemonohydrate |
| 2.0 g | citric acid, free of water |
| 0.1 g | formaldehyde, 35% percent |
| 40.0 g | lauryl alcohol-diglycol ether sulfate, sodium salt (28% percent watery solution) |
| 3.5 g | sodium chloride |
| 46.4 g | water |
| 100.0 g | |

Human hair, which was washed with a shampoo of the aforementioned composition and which was subsequently rinsed, showed a very good wet combability. Furthermore, the pH-value of the shampoo is stabilised by the betaine contained in this shampoo which acts against a rapid drying out of the scalp.

All percentage numbers stated in the application represent weight percentages.

We claim:

1. A hair treatment composition to be used for the strengthening and conditioning of human hair and comprising
    (a) 0.1 to 25.0 percent by weight of trimethylammoiaacetate betaine of the formula $(CH_3)_3-N^{\oplus}-CH_2-COO^{\ominus}$
    (b) 0.1 to 10.0 percent by weight of an aliphatic organic acid selected from the group consisting of tartaric acid, lactic acid, pimelic acid, glyoxylic acid and citric acid; and
    (c) further usual components for hair treatment compositions selected from the group consisting of anionic, cationic, amphorteric or nonionogenic tensides, natural, modified natural or synthetic polymers, thickeners, coloring agents, pigments, perfume oils, antioxidants and preservatives.

2. A hair treatment composition to be used for the strengthening and conditioning of human hair and comprising
    (a) 3.0 to 15.0 percent by weight of trimethylammoniaacetate betaine of the formula $(CH_3)_3-N^{\oplus}-CH_2-COO^{\ominus}$;
    (b) 0.1 to 5.0 percent by weight of citric acid; and
    (c) further usual components for hair treatment compositions, selected from the group consisting of anionic, cationic, amphoteric or nonionogenic tensides, natural, modified natural or synthetic polymers, thickeners, coloring agents, pigments, perfume oils, antioxidants and preservatives.

* * * * *